(12) United States Patent
Messana et al.

(10) Patent No.: US 9,868,689 B2
(45) Date of Patent: *Jan. 16, 2018

(54) ANAEROBIC CURABLE COMPOSITIONS CONTAINING BLOCKED (METH)ACRYLATE ACID COMPOUNDS

(71) Applicant: Henkel IP & Holding GmbH, Duesseldorf (DE)

(72) Inventors: Andrew D. Messana, Newington, CT (US); Sean M. Burdzy, Hamden, CT (US); Joel D. Schall, Hamden, CT (US); Anthony F. Jacobine, North Haverhill, NH (US)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/340,285

(22) Filed: Nov. 1, 2016

(65) Prior Publication Data
US 2017/0044087 A1 Feb. 16, 2017

Related U.S. Application Data

(63) Continuation of application No. PCT/US2015/028829, filed on May 1, 2015.

(60) Provisional application No. 62/088,952, filed on Dec. 8, 2014, provisional application No. 62/061,389, filed on Oct. 8, 2014, provisional application No. 61/987,201, filed on May 1, 2014.

(51) Int. Cl.
| | |
|---|---|
| C08F 20/06 | (2006.01) |
| C08F 118/02 | (2006.01) |
| C07C 69/34 | (2006.01) |
| C09J 4/00 | (2006.01) |
| C07C 229/26 | (2006.01) |
| C08F 222/20 | (2006.01) |
| C09J 135/02 | (2006.01) |
| C08F 220/18 | (2006.01) |
| C08K 5/11 | (2006.01) |
| C08K 5/17 | (2006.01) |

(52) U.S. Cl.
CPC ............ *C07C 69/34* (2013.01); *C07C 229/26* (2013.01); *C08F 222/20* (2013.01); *C09J 4/00* (2013.01); *C09J 135/02* (2013.01); C08F 220/18 (2013.01); C08K 5/11 (2013.01); C08K 5/175 (2013.01)

(58) Field of Classification Search
CPC .... C08F 2/44; C08F 220/28; C08F 2220/281; C08F 2220/286; C08F 222/06; C09J 133/06; C09J 133/14; C08L 33/06; C07C 69/60; C07C 69/54
USPC ............................................... 526/317.1, 319
See application file for complete search history.

(56) References Cited

U.S. PATENT DOCUMENTS

| | | | |
|---|---|---|---|
| 3,970,505 | A | 7/1976 | Hauser et al. |
| 4,215,209 | A | 7/1980 | Meier et al. |
| 4,287,350 | A | 9/1981 | Huellstrung et al. |
| 4,321,349 | A | 3/1982 | Rich |
| 4,324,349 | A | 4/1982 | Kaufman |
| 4,525,232 | A | 6/1985 | Rooney et al. |
| 5,411,988 | A | 5/1995 | Bockow et al. |
| 5,605,999 | A | 2/1997 | Chu |
| 6,048,587 | A | 4/2000 | Estrin |
| 7,728,092 | B1 | 6/2010 | Jacobine et al. |
| 7,951,884 | B1 | 5/2011 | Birkett et al. |
| 2005/0101689 | A1* | 5/2005 | Woods ............. C08F 20/28 522/178 |
| 2009/0281335 | A1 | 11/2009 | Messana et al. |
| 2012/0168219 | A1 | 7/2012 | Kitamura et al. |
| 2013/0289205 | A1* | 10/2013 | Sugasaki .......... B41N 1/12 524/854 |
| 2014/0004353 | A1 | 1/2014 | Birkett et al. |

FOREIGN PATENT DOCUMENTS

| | | |
|---|---|---|
| WO | 9901484 | 1/1999 |
| WO | 2009014688 | 1/2009 |
| WO | 2011047123 | 4/2011 |
| WO | 2014043720 | 3/2014 |

OTHER PUBLICATIONS

International Search Report issued in connection with International Patent Application No. PCT/US2015/028908 dated Aug. 27, 2015.
R.D. Rich, "Anaerobic Adhesives" in Handbook of Adhesive Technology, 29, 467-79, A. Pizzi and K.L. Mittal, eds., Marcel Dekker, Inc., New York (1994) Marcel.
International Search Report issued in connection with International Patent Application No. PCT/US2015/028829 dated Jun. 22, 2015.
International Search Report issued in connection with International Patent Application No. PCT/US2015/028822 dated Jun. 29, 2015.

\* cited by examiner

*Primary Examiner* — William Cheung
(74) *Attorney, Agent, or Firm* — Steven C. Bauman

(57) ABSTRACT

Anaerobic curable compositions, such as adhesives and sealants, containing blocked carboxylic acid compounds are provided. The blocked carboxylic acid compounds are labile carboxylic acid compounds having acetal linkages, which cleave to release the underlying carboxylic acid during anaerobic cure.

10 Claims, No Drawings ns
ANAEROBIC CURABLE COMPOSITIONS CONTAINING BLOCKED (METH)ACRYLATE ACID COMPOUNDS

This application is a continuation of PCT International Application No. PCT/US2015/028829 filed May 1, 2015, which claims priority to U.S. Provisional Patent Application No. 62/088,952 filed Dec. 8, 2014, U.S. Provisional Patent Application No. 62/061,389 filed Oct. 8, 2014, and Provisional Patent Application No. 61/787,201 filed May 1, 2014, each of which is incorporated by reference herein in its entirety.

BACKGROUND

Field

Anaerobic curable compositions, such as adhesives and sealants, containing blocked carboxylic acid compounds are provided. The blocked carboxylic acid compounds are labile carboxylic acid compounds having acetal linkages, which cleave to release the underlying carboxylic acid during anaerobic cure.

Brief Description of Related Technology

Anaerobic adhesive compositions generally are well-known. See e.g., R. D. Rich, "Anaerobic Adhesives" in Handbook of Adhesive Technology, 29, 467-79, A. Pizzi and K. L. Mittal, eds., Marcel Dekker, Inc., New York (1994), and references cited therein. Their uses are legion and new applications continue to be developed.

Conventional anaerobic adhesive compositions ordinarily include a free-radically polymerizable acrylate ester monomer, together with a peroxy initiator and an inhibitor component. Oftentimes, such anaerobic adhesive compositions also contain accelerator components to increase the speed with which the composition cures. Additionally, such compositions may also include adhesion promoters, which can function to increase adhesion to substrates, thereby enhancing adhesive strength.

Maleic acid ("MA") is commonly used together with acetyl phenylhydrazine ("APH") to accelerate cure in anaerobic adhesive compositions. However, MA has limited solubility in some of these compositions, a prime example of which is LOCTITE 243, commercially available from Henkel Corporation, Rocky Hill, Conn.

In addition to its solubility limits, MA has the disadvantage of being heavily regulated due to its health and safety profile, and thus, requires special considerations during handling, storage, and disposal.

As a result of its limited solubility and regulatory scrutiny in certain parts of the world, efforts have been undertaken to identify replacements for MA. To date, these efforts have not provided an acceptable alternative.

It would thus be advantageous to enjoy the properties conferred upon anaerobic curable compositions by MA without the attendant environmental and safety concerns and sparing solubility properties. The present invention provides such a solution.

SUMMARY

In a broad sense, the present invention relates to anaerobic curable compositions, such as adhesives and sealants, containing blocked carboxylic acid compounds. The blocked carboxylic acid compounds are labile carboxylic acid compounds having acetal linkages, which cleave to release the underlying carboxylic acid during anaerobic cure.

A labile carboxylic acid compound ("LCA") is a reaction product that has been prepared from a carboxylic acid and a compound containing at least one vinyl ether group. The so-formed reaction product provides an acetal compound having a structure represented by:

$$[A]_n(CO_2R)_q \qquad \text{I}$$

where A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be; R is an acetal residue; n is 0-5; and q is 1-5.

In structure I the acetal bond(s) is(are) cleavable, and once cleaved release the underlying carboxylic acid to which a vinyl ether containing compound had been reacted to form the acetal blocking unit.

Generally, as noted above, MA is useful as an accelerator in anaerobic curable compositions. The LCA compounds are likewise useful as accelerators for anaerobic curable compositions, such as adhesives and sealants. The LCA compounds can assist to accelerate cure when exposed to anaerobic conditions appropriate to cure the composition. Some of the LCA compounds are useful as chelators, too. The blocking group is removed under the reaction conditions of anaerobic cure, thereby releasing the underlying carboxylic acid to perform its cure accelerating or chelating function. In other words, anaerobic cure conditions cause the cleavage of the acetal bond(s) and re-formation of the underlying carboxylic acid and the vinyl ether compound.

In one aspect, there is provided an anaerobic curable composition which includes:
  a (meth)acrylate component;
  an anaerobic cure system; and
  a compound within structure I.

In another aspect, there is provided an anaerobic curable composition comprising the reaction product of:
  a (meth)acrylate component;
  an anaerobic cure system; and
  a compound within structure I.

In another aspect, there is provided a method of anaerobically curing an anaerobic curable composition which includes:
  (i) providing a composition which includes:
  a (meth)acrylate component;
  an anaerobic cure system; and
  a compound within structure I;
  (ii) applying the composition of (i) to at least a portion of at least one surface of at least one substrate available for bonding;
  (iii) providing another substrate having a surface available for bonding in a mating relationship with the substrate of (ii); and
  (iv) exposing the at least one substrate of (ii) and the substrate of (iii) to anaerobic cure conditions appropriate to cure the composition and bond the substrates.

DETAILED DESCRIPTION

The term "labile carboxylic acid" or LCA is intended to include compounds which undergo a chemical change and revert to its starting materials, a carboxylic acid, such as maleic acid or itaconic acid, and a vinyl ether compound, during anaerobic cure. This term is used interchangeably with "blocked carboxylic acid".

As noted above, the LCA should have a structure represented by:

$$[A]_n(CO_2R)_q \quad \text{I}$$

where A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be; R is an acetal residue; n is 0-5; and q is 1-5.

More specifically, within structure I are LCA compounds having a structure represented by:

II where A and $R_1$ are each independently selected from $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be; n is 0-5; and q is 1-5.

The underlying carboxylic acid therefore may be represented by $$[A]_n(CO_2H)_q \quad \text{III}$$

where A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be; n is 0-5; and q is 1-5.

Embraced by structure III therefore are compounds where n=0, oxalic acid, and where n=1 saturated carboxylic acids, such as where A is 1 carbon atom like malonic acid; where A is 2 carbon atoms like succinic acid; where A is 3 carbon atoms like glutaric acid; where A is 4 carbon atoms like apidic acid; where A is 5 carbon atoms like pimelic acid; where A is 6 carbon atoms like suberic acid; where A is 7 carbon atoms like azelaic acid; and where A is 8 carbon atoms like sebacic acid.

The carboxylic acid compounds have one or more carboxylic acid functional groups consistent with the definitions of structures I, II and III.

Examples of tricarboxylic acid compounds include:

Citric acid

Isocitric acid
CAS 320-77-4 cis-Aconitic acid trans-Aconitic acid 1,2,3-propane tricarboxylic acid
CAS 99-14-9

Trimesic acid

The counterpart LCA compounds for these tricarboxylic acids are thus:

II.3.A

II.3.B

II.3.C

II.3.D

II.3.E

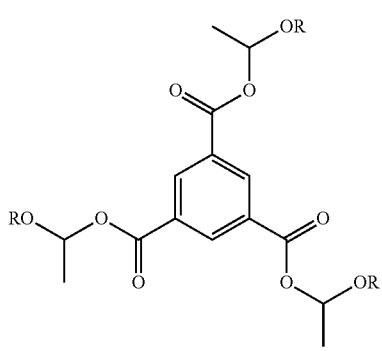

where R in each instance may be the same or different and may be selected from are each independently selected from $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be.

More specific examples of the counterpart LCA compounds for the tricarboxylic acids include

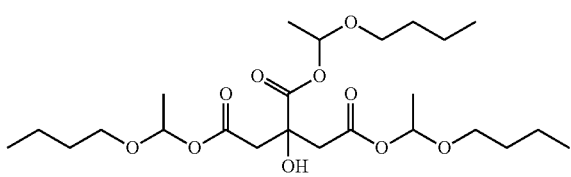

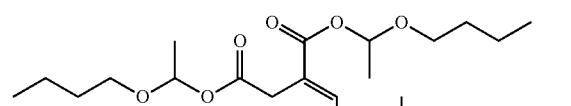

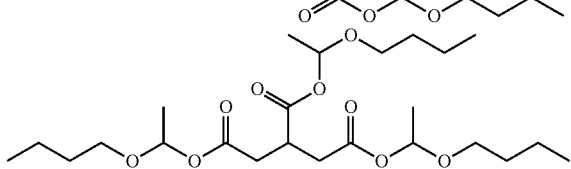

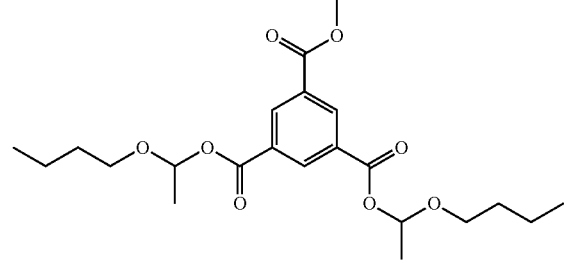

In each of these specific examples, the blocking unit was formed from n-butyl vinyl ether.

Examples of tetracarboxylic acid compounds include:

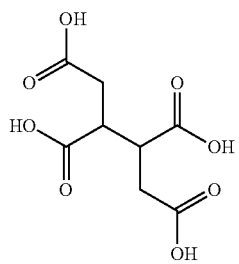

1,2,3,4-Butane tetracarboxylic acid
CAS 1703-58-8

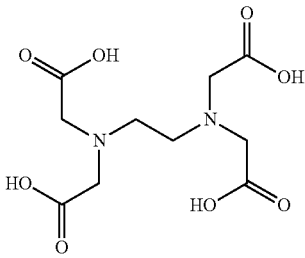

Ethylene glycol bis (2-aminoethyl) tetracetic acid
CAS 60-00-4

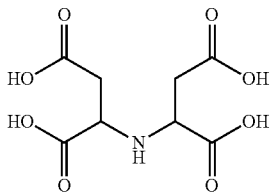

2,2'-Imidosuccinate
CAS 7408-20-0, 70543-06-5 (stereospecific)

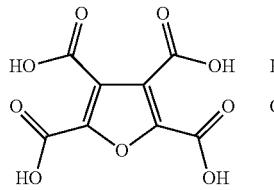 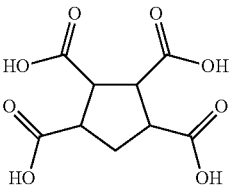

Furan tetracarboxylic acid    Cylcopentane 1,2,3,4-
CAS 20416-04-0                tetracarboxylic acid
                              CAS 3786-91-2

The counterpart LCA compounds for these tetracarboxylic acids are thus:

II.4.A

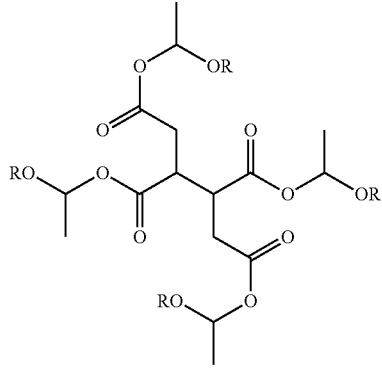

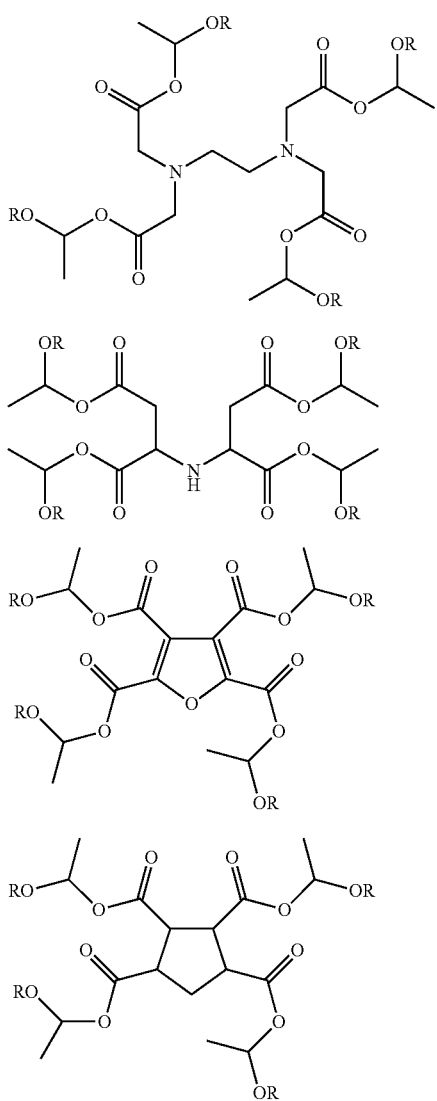

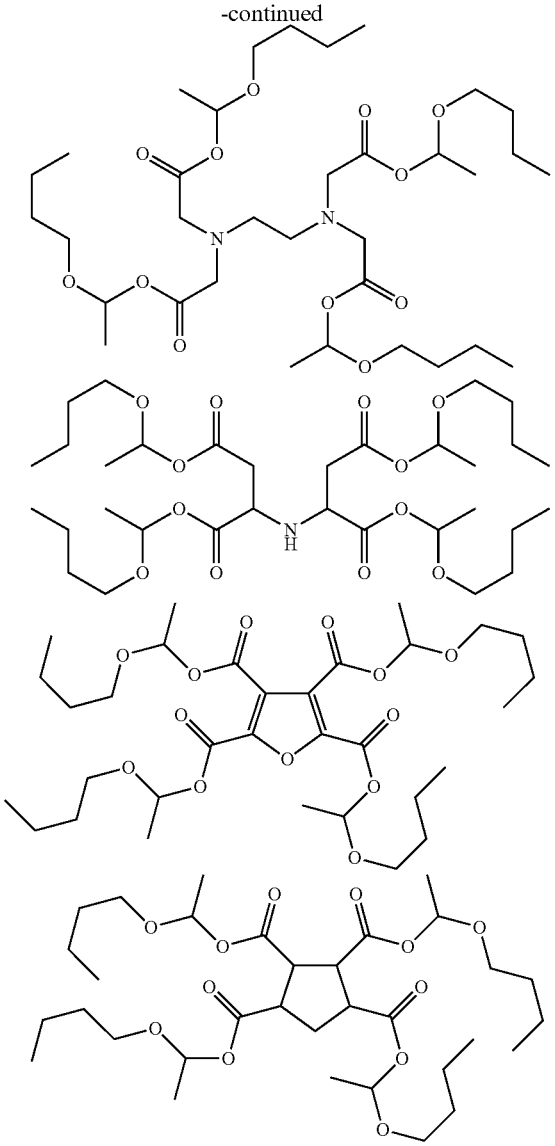

where here R in each instance may be the same or different and may be selected from are each independently selected from $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be.

More specific examples of the counterpart LCA compounds for the tetracarboxylic acids include

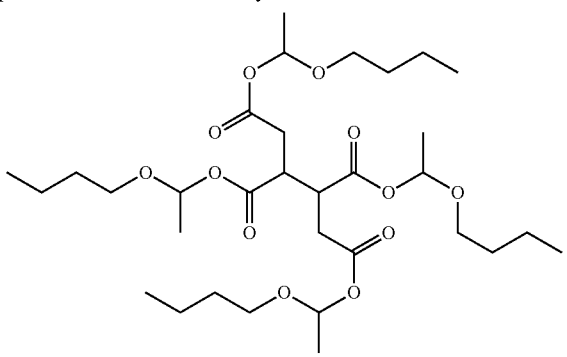

In each of these specific examples, the blocking unit was formed from n-butyl vinyl ether.

The selection of a blocking unit to form the LCA compound is based on several considerations. One such consideration is the ability to "protect" or block the carboxylic acid group such that it prevents premature reaction with its surroundings, thereby alleviating health, safety and environmental concerns, all of which require special handling. Thus, the labile compound should be relatively stable under what would be generally considered normal storage, shelf life and manufacturing conditions for reactant ingredients.

This stability should however not prevent the cleavage of the blocking unit and reformation of underlying carboxylic acid during anaerobic cure. Thus, during preparation and storage of the LCA, the LCA remains substantially stable, and when incorporated into an anaerobic curable composition, this stability continues until the composition is subjected to anaerobic curing conditions. When subjected to anaerobic curing conditions the underlying carboxylic acid becomes unblocked and the underlying carboxylic acid is released to participate in the anaerobic cure. To achieve these properties, the underlying carboxylic acid is joined to the blocking unit—the chosen vinyl ether—via an acetyl lineage.

Another consideration for selection of appropriate blocking units is the compatibility of the LCA with the anaerobic curable composition to which it will be added. Generally, the chosen LCA has good miscibility and/or solubility with (meth)acrylate monomers or resins that form the matrix of the anaerobic curable composition and does not react prematurely to any significant extent with any portion of the anaerobic curable composition. Moreover, once the blocking unit and the underlying carboxylic acid are separated, the blocking unit should not substantially deleteriously affect the anaerobic cure or substantially deleteriously affect the properties of the anaerobic curable composition or the final properties of the cured composition.

Desirably the underlying carboxylic acid is in liquid form or readily miscible and/or soluble with (meth)acrylate monomers or resins for ease of incorporation into the anaerobic curable composition. However, once the LCA is unblocked during anaerobic cure, the vinyl ether compound which acted as a blocking agent is available to participate in the anaerobic cure.

Desirable blocking units include vinyl ether ("VE") compounds. Mono- and di-VE compounds are contemplated, non-limiting examples of which include those listed in Table I below. The VE compounds may be used individually or in combination.

TABLE I

| VE No. | Compound | CAS No. | Structure |
|---|---|---|---|
| 1 | Ethyl vinyl ether | 109-92-2 | 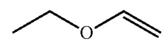 |
| 2 | Isobutyl vinyl ether | 109-53-5 | 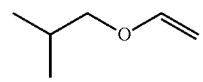 |
| 3 | N-Butyl vinyl ether | 111-34-2 | 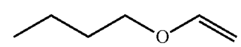 |
| 4 | tert-Butyl vinyl ether | 926-02-3 | 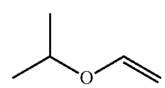 |
| 5 | Cyclohexyl vinyl ether | 2182-55-0 | 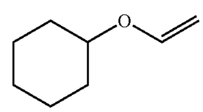 |
| 6 | 1,4-Cyclohexane dimethanol divinyl ether | 17351-75-6 | 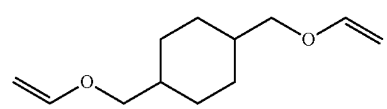 |
| 7 | Butanediol divinyl ether | 3891-33-6 | 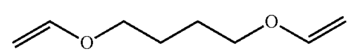 |
| 8 | Hydroxybutyl vinyl ether | 17832-28-9 | 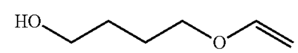 |
| 9 | Diethylene glycol divinyl ether | 764-99-8 | 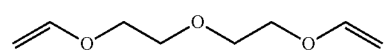 |
| 10 | Triethylene glycol divinyl ether | 765-12-8 | 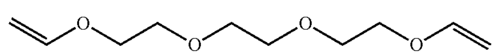 |
| 11 | Dodecyl vinyl ether | 765-14-0 | 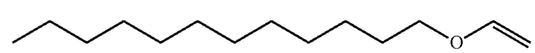 |
| 12 | Octadecyl vinyl ether | 930-02-9 | 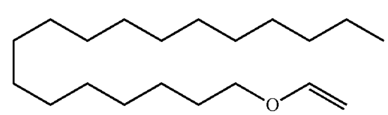 [SMILES: C=COCCCCCCCCCCCCCCCCCC] |
| 13 | 4-(Hydroxy methyl) cyclohexyl methyl vinyl ether | 114651-37-5 | 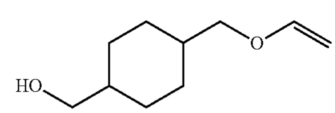 |
| 14 | 2-Ethyl hexyl vinyl ether | 103-44-6 | 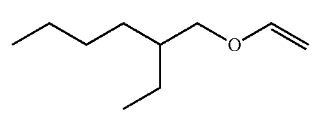 |
| 15 | Diethylene glycol monovinyl ether | 929-37-3 | 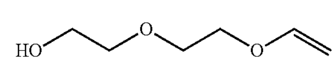 |

TABLE I-continued

| VE No. | Compound | CAS No. | Structure |
|---|---|---|---|
| 16 | Poly-THF 290-Divinyl ether | 486438-23-7 | 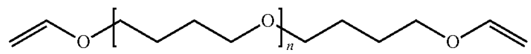 |
| 17 | 3-Amino propyl vinyl ether | 66415-55-2 | 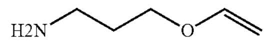 |
| 18 | Tert-Amyl vinyl ether | 29281-39-8 | 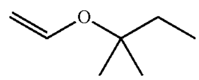 |
| 19 | Diethylaminoethyl vinyl ether | 3205-13-8 | 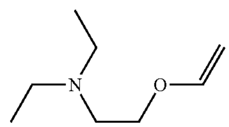 |
| 20 | Ethyleneglycol butyl vinyl ether | 4223-11-4 | 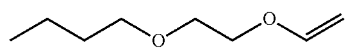 |
| 21 | Ethyleneglycol divinyl ether | 764-78-3 | 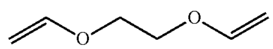 |
| 22 | Ethyleneglycol monovinyl ether | 764-48-7 | 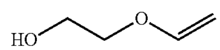 |
| 23 | Hexanediol divinyl ether | 19763-13-4 | 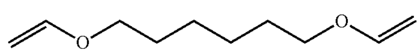 |
| 24 | Hexanediol monovinyl ether | 27336-16-9 | 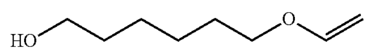 |
| 26 | Isopropyl vinyl ether | 926-65-8 | 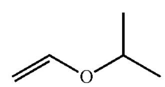 |
| 27 | Polyethyleneglycol-520 methyl vinyl ether | 50856-25-2 | $CH_2=CHO[CH_2CH_2O]_nCH_3$ |
| 28 | Pluriol-E200 divinyl ether | 50856-26-3 | $CH_2=CHO[CH_2CH_2O]_nCH=CH_2$ |
| 29 | n-Propyl vinyl ether | 764-47-6 | 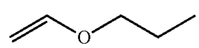 |
| 30 | Tetraethyleneglycol divinyl ether | 83416-06-2 | 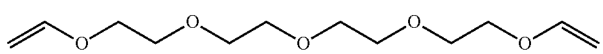 [SMILES: C=COCCOCCOCCOCCOC=C] |
| 31 | Triethyleneglycol methyl vinyl ether | 26256-87-1 | 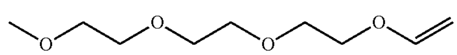 |
| 32 | Trimethylolpropane trivinyl ether | 57758-90-4 | 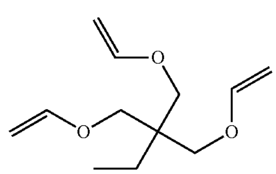 |

The following reaction schemes represent examples of a reaction used to prepare a LCA

1,2,3-propane tricarboxylic acid
CAS 99-14-9

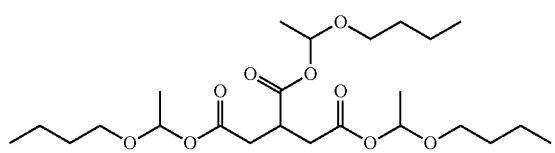

Butyl vinyl ether
CAS 11-34-2

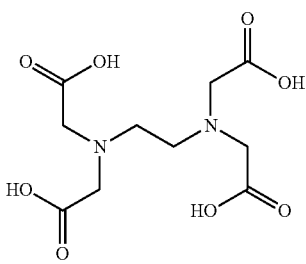

Ethylene glycol bis (2-aminoethyl) tetraacetic acid
CAS 60-00-4

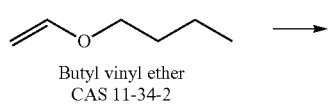

Butyl vinyl ether
CAS 11-34-2

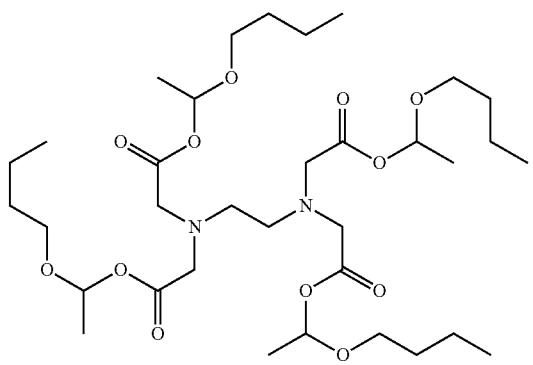

The anaerobic curable composition is based on the (meth) acrylate component, together with an anaerobic cure system, and of course the LCA.

Suitable (meth)acrylate monomers may be chosen from a wide variety of materials, such as those represented by $H_2C=CGCO_2R^1$, where G may be hydrogen, halogen, or alkyl groups having from 1 to about 4 carbon atoms, and $R^1$ may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone, and the like.

Other (meth)acrylate monomers may also be used, such as reaction products of the diglycidylether of bisphenol-A with methacrylic acid and a (meth)acrylate ester corresponding to structure as shown below:

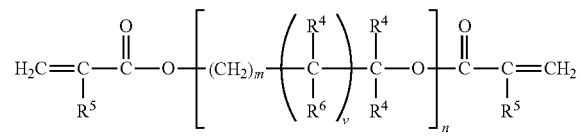

where $R^4$ may be selected from hydrogen, alkyl groups having from 1 to about 4 carbon atoms, hydroxyalkyl groups having from 1 to about 4 carbon atoms or

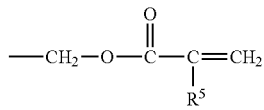

$R^5$ may be selected from hydrogen, halogen, and alkyl groups of from 1 to about 4 carbon atoms;

$R^6$ may be selected from hydrogen, hydroxy and

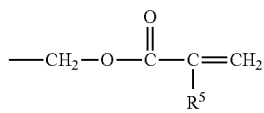

m is an integer equal to at least 1, e.g., from 1 to about 8 or higher, for instance, from 1 to about 4; v is 0 or 1; and n is an integer equal to at least 1, e.g., 1 to about 20 or more.

Still other (meth)acrylate monomers include silicone (meth)acrylates ("SiMA"), such as those taught by and claimed in U.S. Pat. No. 5,605,999 (Chu), the disclosure of which is hereby expressly incorporated herein by reference.

Additional (meth)acrylate monomers include polyfunctional (meth)acrylate monomers, such as, but not limited to, di- or tri-functional (meth)acrylates like polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylate ("TMPTMA"), diethylene glycol dimethacrylate, triethylene glycol dimethacrylate ("TRIEGMA"), tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate and bisphenol-A mono and di(meth)acrylates, such as ethoxylated bisphenol-A (meth)acrylate ("EBIPMA"), and bisphenol-F mono and di(meth)acrylates, such as ethoxylated bisphenol-F (meth)acrylate.

Combinations of (meth)acrylate monomers may also be used.

The (meth)acrylate component may be present in an amount from about 10 to about 90 percent by weight, such as from about 60 to about 90 percent by weight, based on the total weight of the composition.

Additional components have been included in traditional anaerobic curable compositions to alter the physical properties of either the curable compositions or reaction products thereof, and such additional components may be used in the so-described anaerobic curable compositions.

For instance, one or more of thermal resistance-conferring coreactants (such as maleimides), diluent components reactive at elevated temperature conditions, mono- or polyhydroxyalkanes, polymeric plasticizers, and chelators (see International Patent Application No. PCT/US98/13704, the disclosure of which is hereby expressly incorporated herein by reference) may be included to modify the physical properties and/or cure profile of the formulation and/or the strength or temperature resistance of the cured adhesive.

When used, the coreactant, reactive diluent, plasticizer, and/or mono- or poly-hydroxyalkanes, may be present in an amount within the range of about 1 percent to about 30 percent by weight, based on the total weight of the composition.

The anaerobic cure system includes a free-radical initiator, such as a peroxide, and optionally, one or more components selected from free-radical accelerators, free-radical inhibitors, as well as metal catalysts, such as iron and copper.

A number of well-known initiators of free radical polymerization are typically incorporated into anaerobic curable compositions including hydroperoxides, such as cymene hydroperoxides ("CHP"), para-menthane hydroperoxide, t-butyl hydroperoxide ("TBH") and t-butyl perbenzoate. Other initiators of free radical polymerization include peroxides, such as benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, cumene hydroperoxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10% by weight, based on the total weight of the composition, with about 1 to 5% being desirable.

Accelerators of free radical polymerization may also be used in the compositions of the present invention including, without limitation, organic amides and imides, such as benzoic sulfimide (also known as saccharin) (see U.S. Pat. No. 4,324,349). Such accelerators may also be of the hydrazine variety (e.g., acetyl phenyl hydrazine, APH), as disclosed in U.S. Pat. No. 4,287,350 (Rich) and U.S. Pat. No. 4,321,349 (Rich). Conventionally, MA is often added to APH-containing anaerobic cure systems. Here, instead of MA, a LCA is useful instead. Additional specific accelerators include, without limitation, N,N-diethyl-p-toluidine ("DE-p-T") and N,N-dimethyl-o-toluidine ("DM-o-T"). Additional classes of accelerators include thiocaprolactams (e.g., U.S. Pat. No. 5,411,988) and throureas (e.g., U.S. Pat. No. 3,970,505).

When used, accelerators such as saccharin may be present in amounts of about 0.5% to 5% by weight of the total composition.

Stabilizers and inhibitors (such as phenols including hydroquinone and quinones) may also be employed to control and prevent premature peroxide decomposition and polymerization of the composition of the present invention.

Chelating agents, such as the tetrasodium salt of ethylenediamine tetraacetic acid ("EDTA"), may be used to trap trace amounts of metal contaminants. When used, chelating agents may ordinarily be present in the compositions in an amount from about 0.001% by weight to about 0.1% by weight, based on the total weight of the composition.

Metal catalyst solutions or pre-mixes thereof may be used in amounts of about 0.03 to about 0.1% by weight based on the total weight of the composition.

Thickeners, plasticizers, fillers, toughening agents (such as elastomers and rubbers) and other well-known additives may be incorporated herein where the skilled artisan believes it would be desirable to do so.

Also provided are methods of preparing and using the anaerobic curable compositions, as well as reaction products of the compositions.

The anaerobic curable compositions may be prepared using conventional methods that are well known to those persons of skill in the art. For instance, the components may be mixed together in any convenient order consistent with the roles and functions the components are to perform in the compositions. Conventional mixing techniques using known apparatus may be employed.

The anaerobic curable compositions may be applied to a variety of substrates to perform with the desired benefits and advantages described herein. For instance, appropriate substrates may be constructed from steel, brass, copper, aluminum, zinc, and other metals and alloys, ceramics, and thermosets. The compositions of this invention demonstrate particularly good bond strength on surfaces commonly referred to as "active" surfaces, such as iron, brass and copper. An appropriate primer for anaerobic curable compositions may be applied to a surface of the chosen substrate to enhance cure rate.

In addition, a method of preparing an anaerobic curable composition is provided, a step of which includes mixing together a (meth)acrylate component, an anaerobic cure system, and an LCA.

Also provided is a process for bonding using the anaerobic curable composition, the steps of which include applying the composition to a desired substrate surface and exposing the composition to an anaerobic environment for a time sufficient to cure the composition.

In view of the above description, it is clear that a wide range of practical opportunities are provided. The following examples are for illustrative purposes only, and are not to be construed so as to limit in any way the teaching herein.

EXAMPLES

Example 1

Synthesis

Among the more desirable VE compounds is n-butyl vinyl ether. The selection of n-butyl vinyl ether as the blocking unit provides the following reaction scheme with 1,3-propane tricarboxylic acid or ethylene glycol bis(2-aminoethyl) tetraacetic acid:

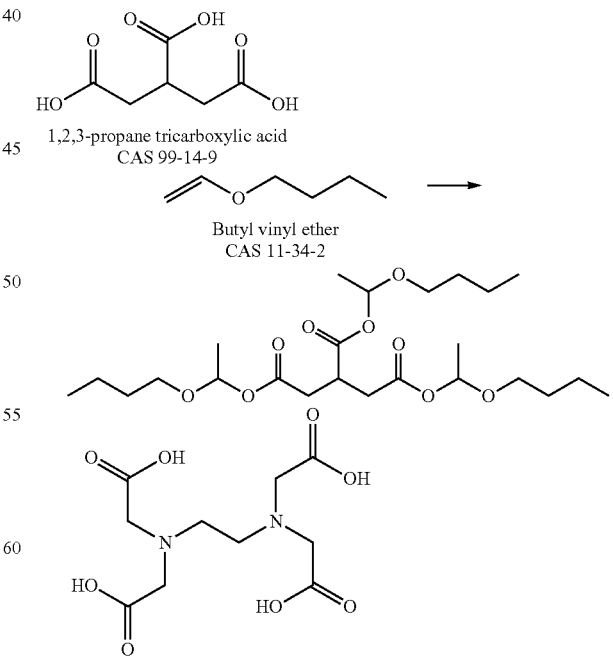

-continued

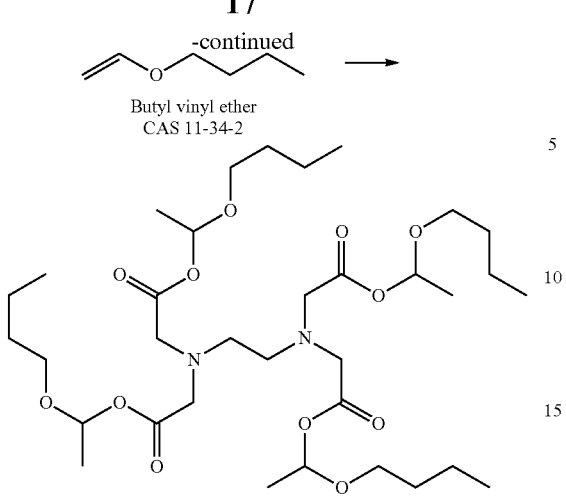

Butyl vinyl ether
CAS 11-34-2

1,2,3-Propane tricarboxylic acid (52.8 g, 300 mmol) and heptane (150 mL) is added to a 1000 mL 3-neck round bottom flask ("RBF") equipped with magnetic stirring, nitrogen purge, thermo-controlling, pressure-equilibrated addition funnel, and condenser. Butyl vinyl ether (92.0 g, 900 mmol) is added over a few minutes at ambient temperature. Heptane (150 mL) is then added to the RBF. The mixture is warmed to a temperature of 60° C.

The reaction is monitored by FT-IR until complete, at which point the reaction is twice washed with water (150 mL), separated, dried over anhydrous magnesium sulfate, gravity filtered, and concentrated in vacuo and under a reduced pressure.

Ethylene glycol bis (2-aminoethyl) tetra acetic acid (58.5 g, 200 mmol) and heptane (100 mL) is added to a 500 mL 3-neck RBF equipped with magnetic stirring, nitrogen purge, thermo-controlling, pressure-equilibrated addition funnel, and condenser. Butyl vinyl ether (81.76 g, 800 mmol) is added over a few minutes at ambient temperature. Heptane (100 mL) is then added to the RBF. The mixture is warmed to a temperature of 60° C.

The reaction is monitored by FT-IR until complete, at which point the reaction is twice washed with water (100 mL), separated, dried over anhydrous magnesium sulfate, gravity filtered, and concentrated in vacuo under a reduced pressure.

What is claimed is:

1. An anaerobic curable composition comprising;
   (a) a (meth)acrylate component;
   (b) an anaerobic cure system; and
   (c) a compound of structure I $$[A\text{---}_n(CO_2R)]_q \quad \text{I}$$

wherein A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively; R is an acetal residue derived from a vinyl ether compound selected from one or more of ethyl vinyl ether; isobutyl vinyl ether; n-butyl vinyl ether; tert-butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tert-amyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether; n is 0-5; and q is 1-5.

2. The composition of claim 1, wherein the compound of structure I is represented by structure II below:

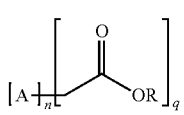

wherein A is selected from $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively; n is 0-5; and q is 1-5.

3. The composition of claim 1 wherein the compound of (c) is the reaction product of a vinyl ether compound and a carboxylic acid.

4. The composition of claim 1 wherein the (meth)acrylate component is represented by:

$H_2C\text{=}CGCO_2R^1$, wherein G may be hydrogen, halogen, or alkyl groups having from 1 to about 4 carbon atoms, and R1 may be selected from alkyl, cycloalkyl, alkenyl, cycloalkenyl, alkaryl, aralkyl, or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate and sulfone;

reaction products of the digiycidylether of bisphenol-A with methacrylic acid and a (meth)acrylate ester corresponding to structure as shown below:

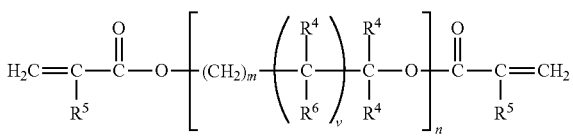

wherein $R^4$ may be selected from hydrogen, alkyl groups having from 1 to about 4 carbon atoms, hydroxyalkyl groups having from 1 to about 4 carbon atoms or

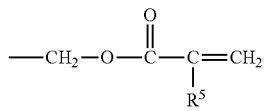

$R^5$ may be selected from hydrogen, halogen, and alkyl groups of from 1 to about 4 carbon atoms;

$R^6$ may be selected from hydrogen, hydroxy and

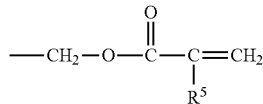

m is an integer equal to at least 1;
v is 0 or 1; and
n is an integer equal to at least 1; and
polyfunctional (meth)acrylate monomers, di- or tri-functional (meth)acrylates, polyethylene glycol di(meth)acrylates, tetrahydrofuran (meth)acrylates and di(meth)acrylates, hydroxypropyl (meth)acrylate, hexanediol di(meth)acrylate, trimethylol propane tri(meth)acrylate, diethylene glycol dimethacrylate, triethylene glycol dimethacrylate, tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate, bisphenol-A mono and di(meth)acrylates, ethoxylated bisphenol-A (meth)acrylate, and bisphenol-F mono and di(meth)acrylates, and ethoxylated bisphenol-F (meth)acrylate.

5. The composition of claim 1 wherein the anaerobic cure system comprises a free-radical initiation and optionally one or more free-radical accelerators.

6. A composition comprising the reaction product of:
   (a) a (meth)acrylate component;
   (b) an anaerobic cure system; and
   (c) a compound of structure $$[A\text{-}]_n(CO_2R)_q \qquad \text{I}$$

wherein A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively; R is an acetal residue derived from a vinyl ether compound selected from one or more of ethyl vinyl ether; isobutyl vinyl ether; n-butyl vinyl ether; tert-butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-TEF 290-divinyl ether; 3-amino propyl vinyl ether; tert-amyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether; n is 0-5; and q is 1-5.

7. A method of making an anaerobic curable composition comprising;
   (i) Providing a composition comprising:
      (a) a (meth)acrylate component; and
      (b) an anaerobic cure system; and
   (ii) Adding to the composition of step (i) a compound of structure I $$[A\text{-}]_n(CO_2R)_q \qquad \text{I}$$

wherein A is $C_{1-12}$ alkyl or alkylene, $C_{2-12}$ alkenyl or alkenylene, $C_{5-14}$ cycloalkyl, $C_{5-14}$ cycloalkenyl, $C_{5-14}$ cycloalkylene, or $C_{5-14}$ cycloalkenylene, or $C_{6-14}$ aryl, each of which may be interrupted or substituted by one or more heteroatoms or heteroatom containing groups, respectively, as the case may be; R is an acetal residue derived from a vinyl ether compound selected from one or more of ethyl vinyl ether; isobutyl vinyl ether; n-butyl vinyl ether; tert-butyl vinyl ether; cyclohexyl vinyl ether; 1,4-cyclohexane dimethanol divinyl ether; butanediol divinyl ether; hydroxybutyl vinyl ether; diethylene glycol divinyl ether; triethylene glycol divinyl ether; dodecyl vinyl ether; octadecyl vinyl ether; 4-(hydroxy methyl) cyclohexyl methyl vinyl ether; 2-ethyl hexyl vinyl ether; diethylene glycol monovinyl ether; poly-THF 290-divinyl ether; 3-amino propyl vinyl ether; tert-amyl vinyl ether; diethylaminoethyl vinyl ether; ethyleneglycol butyl vinyl ether; ethyleneglycol divinyl ether; ethyleneglycol monovinyl ether; hexanediol divinyl ether; hexanediol monovinyl ether; isopropyl vinyl ether; polyethyleneglycol-520 methyl vinyl ether; pluriol-E200 divinyl ether; n-propyl vinyl ether; tetraethyleneglycol divinyl ether; triethyleneglycol methyl vinyl ether; and trimethylolpropane trivinyl ether; n is 0-5; and q is 1-5.

8. The anaerobic curable composition of claim 1, wherein the compound of structure I is chosen from

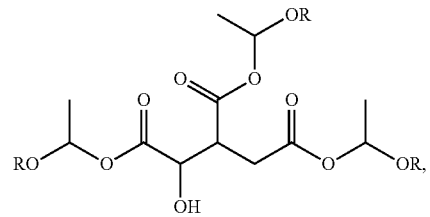

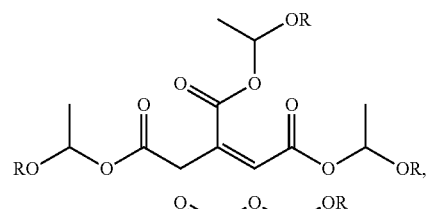

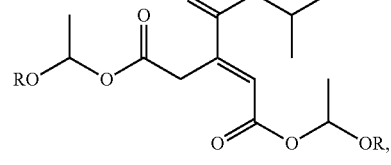

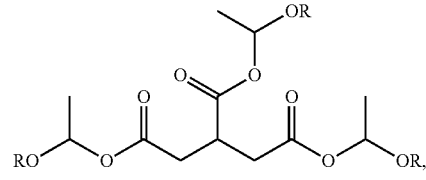

-continued
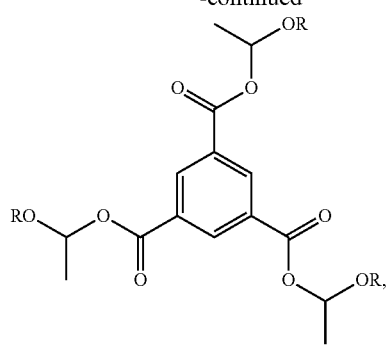
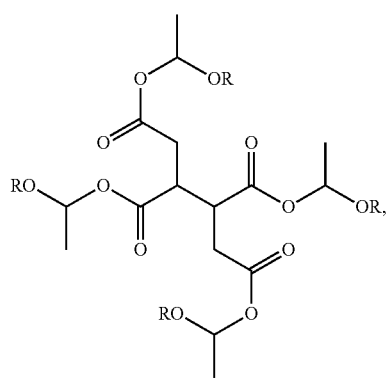
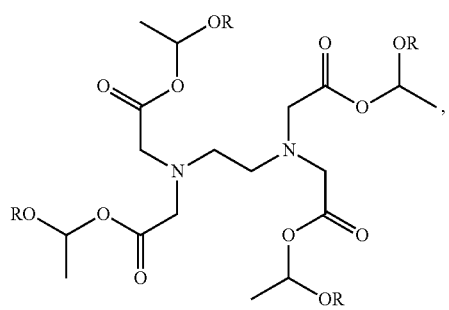
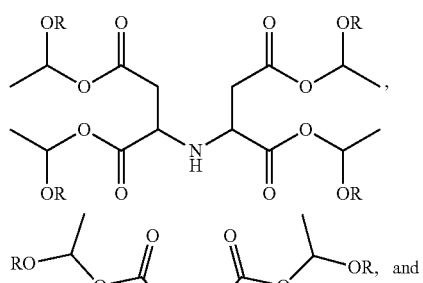
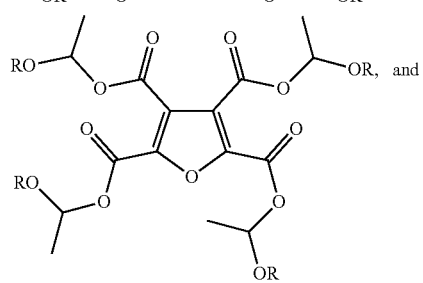
-continued
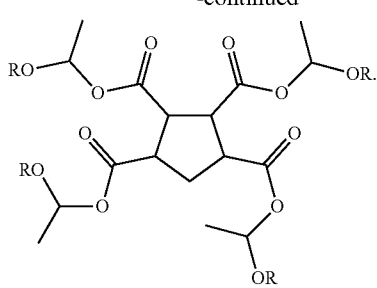
9. The composition of claim 6, wherein the compound of structure I is chosen from
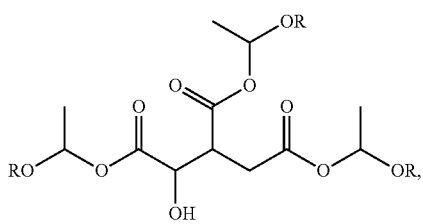
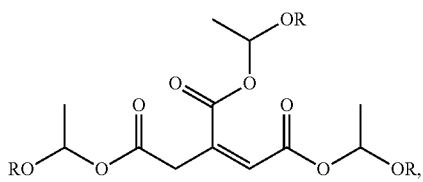
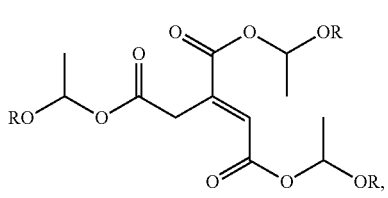
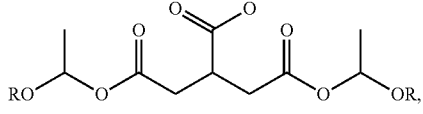
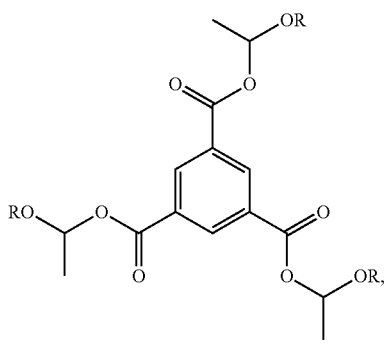

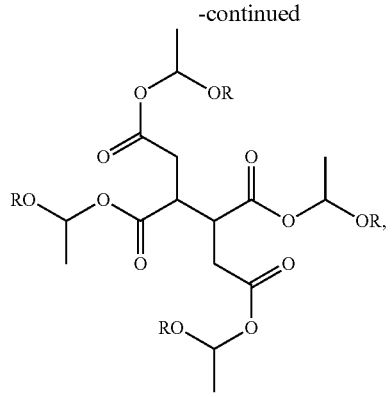
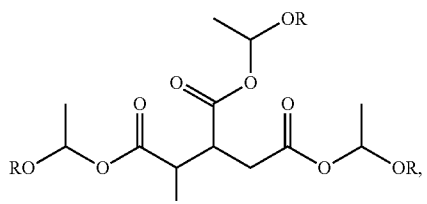
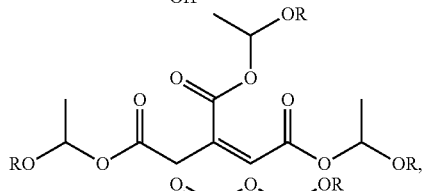
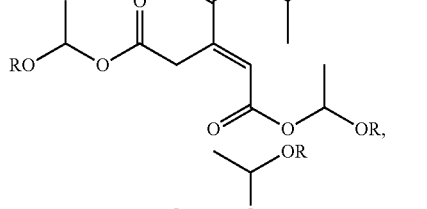
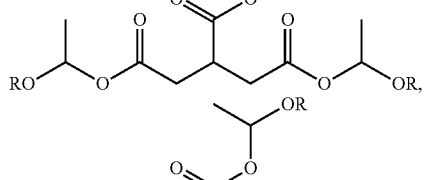
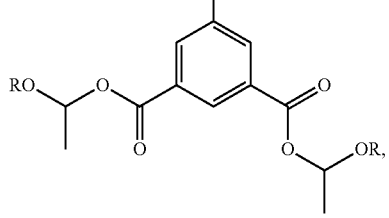
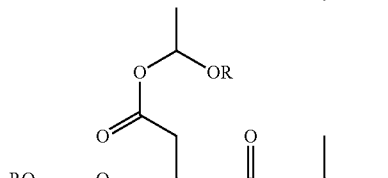
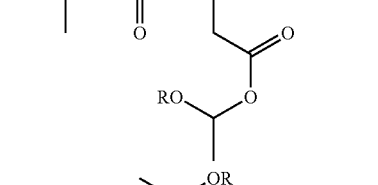
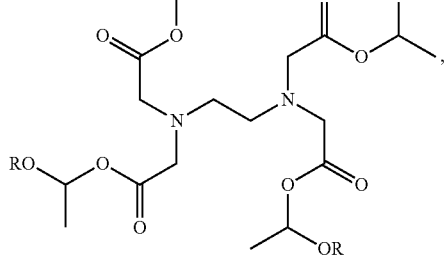
10. The method of claim 7, wherein the compound of structure I is chosen from

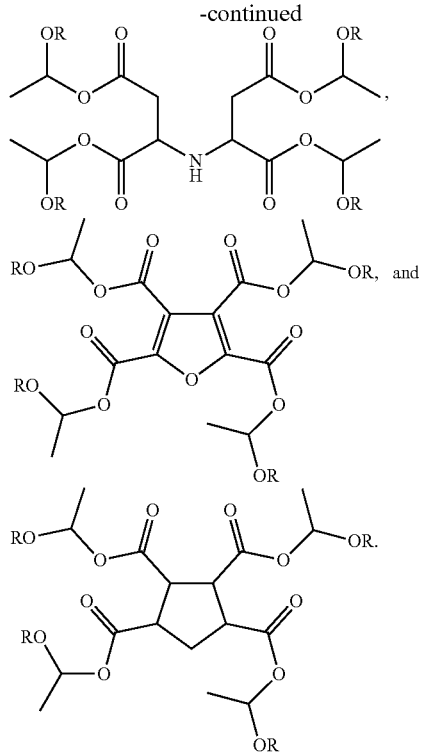
* * * * *

UNITED STATES PATENT AND TRADEMARK OFFICE
CERTIFICATE OF CORRECTION

PATENT NO. : 9,868,689 B2
APPLICATION NO. : 15/340285
DATED : January 16, 2018
INVENTOR(S) : Andrew D. Messana et al.

Page 1 of 1

It is certified that error appears in the above-identified patent and that said Letters Patent is hereby corrected as shown below:

In the Claims

Column 19, Line 53, change "poly- TEF" to -- poly-THF --.

Signed and Sealed this
Nineteenth Day of February, 2019

Andrei Iancu
*Director of the United States Patent and Trademark Office*